United States Patent [19]

Huang et al.

[11] Patent Number: 5,684,195
[45] Date of Patent: Nov. 4, 1997

[54] METHOD OF PREPARING SULFMONAMIDES FROM SULFONES

[75] Inventors: Horng-Chih Huang, Chesterfield, Mo.; Scott R. Harring, Buffalo Grove, Ill.

[73] Assignee: G. D. Searle & Co., Skokie, Ill.

[21] Appl. No.: 455,460

[22] Filed: May 31, 1995

Related U.S. Application Data

[63] Continuation-in-part of Ser. No. 275,183, Jul. 14, 1994, abandoned.

[51] Int. Cl.$^6$ .................................................. C07C 303/36
[52] U.S. Cl. .......................... 564/90; 549/75; 564/84; 564/91; 564/98
[58] Field of Search ........................... 564/84, 90, 91, 564/98; 549/75; 562/125

[56] References Cited

FOREIGN PATENT DOCUMENTS

| | | |
|---|---|---|
| 483928 | 5/1992 | European Pat. Off. |
| 90/13549 | 11/1990 | WIPO |

OTHER PUBLICATIONS

A. Korolkovas, *Essentials of Medicinal Chemistry*, 699–716 (1988).

K. Anderson, *Comprehensive Organic Chemistry*, D. Jones, Ed., vol. 3, 345, 317 (1979).

H. Pinnick et al, *J. Org. Chem.*, 44, 160 (1979).

T. Hamada et al, *Synthesis*, 852 (1986).

F. Scully et al, *J. Org. Chem.*, 46, 5077 (1981).

S. Graham et al, *Synthesis*, 1031 (1986).

E. Negishi et al, *J. Org. Chem.*, 40, 814, 1676 (1975).

E. Negishi et al, *J. Chem. Soc. Perkin Trans.*, 2, 1225 (1978).

T. Mukaiyama et al, *Bull. Chem. Soc. Japan*, 45, 2244 (1972).

R. Hughes et al, *Chem. Soc. Chem Comm.*, 863 (1974).

D. Uguen *Bull. Soc. Chim. Fr.*, 3–4, 99 (1981).

K. McCullough, *Tet. Lett.*, 23:21:2223–4 (1982).

P. Kocienski, *Tet. Lett.*, 28:2649–50 (1979).

M. Ochiai et al, *Tet. Lett.*, 23:21:2205–8 (1982).

*Primary Examiner*—Peter O'Sullivan
*Attorney, Agent, or Firm*—Joseph W. Bulock

[57] ABSTRACT

A one-pot synthesis of sulfonamides from sulfones has been developed. Conversion of sulfones to the corresponding sulfinic acid salts is followed by oxidative-amination to give the sulfonamides.

20 Claims, No Drawings

METHOD OF PREPARING SULFMONAMIDES FROM SULFONES

RELATED CASE

This application is a continuation-in-part of U.S. patent application Ser. No. 08/275,183, filed Jul. 14, 1994 now abandoned.

BACKGROUND OF THE INVENTION

Sulfonamides have been widely used for treatment of bacterial or viral infections, and are also found in drugs such as diuretics, hypoglycemic, antimalarial agents and many others (A. Korolkovas, *Essentials of Medicinal Chemistry*, 699–716 (1988)). The most common synthetic method used to make sulfonamides usually involves the preparation of a sulfonyl chloride from a sulfonic acid and phosphorous pentachloride, followed by treatment with amines [K. Anderson, *Comprehensive Organic Chemistry*, D. Jones, Ed., Vol. 3, 345 (1979)].

Alternatively, aryllithiums (generated from aryl halides and butyllithium) have been reacted with sulfur dioxide to give the corresponding arylsulfinates, [K. Anderson, *Comprehensive Organic Chemistry*, D. Jones, Ed., Vol. 3, 317 (1979)]; H. Pinnick and M. Reynolds, *J. Org. Chem.*, 44, 160 (1979); T. Hamada and O. Yonemitsu, *Synthesis*, 852 (1986)] which are subsequently treated with chloramine or hydroxylamine-O-sulfonic acid to give sulfonamides directly [F. Scully and K. Bowdring, *J. Org. Chem.*, 46, 5077 (1981); S. Graham, and T. Scholz, *Synthesis*, 1031 (1986)]. This process is also described in European Application EP 483,928, published May 6, 1992, and WO 90/13549, published Nov. 15, 1990, for the formation of saccharin derivatives. This process usually is tedious, inconvenient, and often incompatible with other existing functional groups, especially if one wishes to introduce the sulfonamidyl group at a later stage of a multi-step synthesis. Moreover, the versatility of this process also depends on the availability of the appropriate aryl halide.

Trialkylboranes have been known to form "borate" complexes with lithiated organosulfur compounds [E. Negishi, et al, *J. Org. Chem.*, 40, 814 (1975); E. Negishi, et al, *J. Chem. Soc. Perkin Trans.*, 2, 1225 (1978); T. Mukaiyama, et al, *Bull. Chem. Soc. Japan*, 45, 2244 (1972); R. Hughes, et al, *Chem. Soc. Chem. Comm.*, 863 (1974); E. Negishi, et al, *J. Org. Chem.*, 40, 1676 (1975)]. D. Uguen has proposed that the reaction of an anion of a phenyl alkylsulfonyl and tributylborane forms an anionic complex, which rearranges to form a trialkylborane and a phenylsulfinate anion as a side-product [*Bull. Soc. Chim. Fr.*, 3–4, 99 (1981)].

SUMMARY OF THE INVENTION

This invention provides an efficient one-pot synthesis of sulfonamides from widely accessible sulfones (or sulfides or sulfines once oxidized to the sulfones) under very mild reaction conditions. This procedure provides a convenient and general method for modifying sulfonyl compounds which have only one acidic methyl or methylene group. The fact that methylsulfides or methylsulfones are more accessible commercially, and can tolerate a wide variety of common chemical transformation conditions, also suggests that one may use a methylsulfide or methylsulfone as a masked sulfonamide to be carried through multi-step synthesis and demasked later at an appropriate, chosen stage.

DETAILED DESCRIPTION OF THE INVENTION

This invention relates to a method of forming sulfonamides from alkylsulfones and the like.

Specifically, the invention relates to a method of preparing sulfonamides comprising the steps of forming a sulfinic acid salt from a sulfone, and treating said sulfinic acid salt with an aminating agent to form the sulfonamide.

More specifically, the invention relates to a method of preparing sulfonamides of Formula I

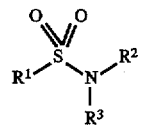

wherein $R^1$ is a radical not attached to the sulfur atom through a methylene radical; and wherein $R^2$ and $R^3$ are independently selected from hydrido, alkyl, alkenyl, aryl and heteroaryl, wherein the aryl and heteroaryl radicals are optionally substituted at a substitutable position with one or more radicals selected from halo, alkyl and alkoxy; said method comprising the steps of converting a sulfone into a sulfinic acid salt, and forming the sulfonamide by treating said sulfinic acid salt with an aminating agent.

Preferably, $R^1$ is selected from phenyl, naphthyl, biphenyl, five or six membered heteroaryl, lower alkyl, lower alkenyl, lower alkynyl and lower cycloalkenyl, wherein $R^1$ is optionally substituted at a substitutable position with one or more radicals selected from halo, lower alkyl, lower alkoxy, five or six membered heteroaryl, phenyl, naphthyl, biphenyl and lower cycloalkenyl; and wherein $R^2$ and $R^3$ are independently selected from hydrido, lower alkyl, lower alkenyl, phenyl and five or six membered heteroaryl, wherein the phenyl and heteroaryl radicals are optionally substituted at a substitutable position with one or more radicals selected from halo, lower alkyl and lower alkoxy.

More preferably, $R^1$ is selected from phenyl, naphthyl, biphenyl, thienyl, pyridyl, thiazolyl, oxazolyl, imidazolyl, pyrazolyl, tert-butyl, ethenyl, 2-propenyl, 3-butenyl, propargyl, 1-cyclopentenyl, 1-cyclohexenyl, 1-cyclobutenyl and 1-cycloheptenyl, wherein $R^1$ is optionally substituted at a substitutable position with one or more radicals selected from fluoro, chloro, bromo, iodo, methoxy, ethoxy, propoxy, butoxy, pentoxy, methylenedioxy, methyl, ethyl, propyl, isopropyl, butyl, iso-butyl, tert-butyl, pentyl, hexyl, thienyl, pyridyl, thiazolyl, oxazolyl, imidazolyl, pyrazolyl, phenyl, naphthyl, cyclobutenyl, cyclopentenyl and cyclohexenyl; and wherein $R^2$ and $R^3$ are independently selected from hydrido, methyl, ethyl, propyl, isopropyl, butyl, iso-butyl, tert-butyl, pentyl, hexyl, ethenyl, propenyl, isopropenyl, butenyl, iso-butenyl, allyl, pentenyl, phenyl and five or six membered heteroaryl selected from thienyl, pyridyl, thiazolyl, oxazolyl, imidazolyl, pyrazolyl, piperidinyl, pyrrolidinyl, morpholinyl and tetrahydroisoquinolinyl, wherein the heteroaryl and phenyl radicals are optionally substituted at a substitutable position with one or more radicals selected from fluoro, chloro, bromo, iodo, methyl, ethyl, propyl, isopropyl, butyl, iso-butyl, tert-butyl, pentyl, hexyl, methoxy, ethoxy, propoxy, butoxy, pentoxy and methylenedioxy.

Even more preferably, $R^1$ is selected from phenyl, thienyl, pyridyl and tert-butyl, wherein $R^1$ is optionally substituted at a substitutable position with one or more radicals selected from fluoro, chloro, bromo, iodo, thienyl, pyridyl, thiazolyl, oxazolyl, imidazolyl, pyrazolyl, phenyl and cyclopentenyl; and wherein $R^2$ and $R^3$ are hydrido.

Even more specifically, the invention relates to a method of preparing sulfonamides of Formula II

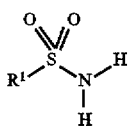

wherein $R^1$ is a radical not attached to the sulfur atom through a methylene radical; said method comprising treating a sulfone of Formula III

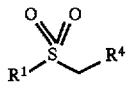

with a base and an alkylborane in an appropriate solvent to form a trialkylborate-sulfone complex, converting said complex into a sulfinic acid salt, and forming said sulfonamide by treating the sulfinic acid salt with an aminating agent; wherein $R^4$ is selected from hydrido, alkyl, aryl, heteroaryl and alkenyl; and wherein any of the foregoing $R^1$ and $R^4$ groups are substituted at one or more substitutable positions with one or more radicals independently selected from halo, alkyl, alkoxy, heteroaryl, aryl and cycloalkenyl.

Preferably, $R^1$ is selected from phenyl, naphthyl, biphenyl, five or six membered heteroaryl, lower alkyl, lower alkenyl, lower alkynyl and lower cycloalkenyl; and $R^4$ is selected from hydrido, lower alkyl, phenyl, naphthyl, five or six membered heteroaryl and lower alkenyl; wherein any of the foregoing $R^1$ and $R^4$ groups are substituted at one or more substitutable positions with one or more radicals independently selected from halo, lower alkyl, lower alkoxy, five or six membered heteroaryl, phenyl and lower cycloalkenyl.

More preferably, $R^1$ is selected from phenyl, naphthyl, biphenyl, thienyl, pyridyl, thiazolyl, oxazolyl, imidazolyl, pyrazolyl, tert-butyl, ethenyl, 2-propenyl, 3-butenyl, propargyl, 1-cyclopentenyl, 1-cyclohexenyl, 1-cyclobutenyl and 1-cycloheptenyl; and $R^4$ is selected from hydrido, methyl, ethyl, propyl, isopropyl, butyl, iso-butyl, tert-butyl, pentyl, hexyl, phenyl, naphthyl, thienyl, pyridyl, thiazolyl, oxazolyl, imidazolyl, pyrazolyl, ethenyl, butenyl and propenyl; wherein any of the foregoing $R^1$ and $R^4$ groups are substituted at one or more substitutable positions with one or more radicals independently selected from fluoro, chloro, bromo, iodo, methoxy, ethoxy, propoxy, butoxy, pentoxy, methylenedioxy, methyl, ethyl, propyl, isopropyl, butyl, iso-butyl, tert-butyl, pentyl, hexyl, thienyl, pyridyl, thiazolyl, oxazolyl, imidazolyl, pyrazolyl, phenyl, cyclobutenyl, cyclopentenyl and cyclohexenyl.

Even more preferably, $R^1$ is selected from phenyl, thienyl, pyridyl and tert-butyl, wherein $R^1$ is optionally substituted at a substitutable position with one or more radicals selected from fluoro, chloro, bromo, iodo, thienyl, pyridyl, thiazolyl, oxazolyl, imidazolyl, pyrazolyl, phenyl and cyclopentenyl; and $R^4$ is selected from hydrido, methyl and phenyl.

In addition, a second more specific method included in the invention relates to a method of preparing sulfonamides of Formula II

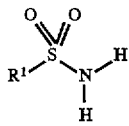

said method comprising treating a sulfone of Formula III

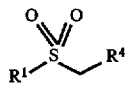

with a base and a substituted trialkylsilane in an appropriate solvent to form a silylalkylsulfone, treating said silylalkylsulfone with an alkylammonium halide to form a sulfinic acid salt, and forming said sulfonamide by treating the sulfinic acid salt with an aminating agent;

wherein $R^1$ is a radical not attached to the sulfur atom through a methylene radical; wherein $R^4$ is selected from hydrido, alkyl, aryl, heteroaryl and alkenyl; and wherein any of the foregoing $R^1$ and $R^4$ groups may be substituted at one or more substitutable positions with one or more radicals independently selected from halo, alkyl, alkoxy, heteroaryl, aryl and cycloalkenyl.

Preferably, $R^1$ is selected from phenyl, naphthyl, biphenyl, five or six membered heteroaryl, lower alkyl, lower alkenyl, lower alkynyl and lower cycloalkenyl; and $R^4$ is selected from hydrido, lower alkyl, phenyl, naphthyl, five or six membered heteroaryl and lower alkenyl; wherein any of the foregoing $R^1$ and $R^4$ groups are substituted at one or more substitutable positions with one or more radicals independently selected from halo, lower alkyl, lower alkoxy, five or six membered heteroaryl, phenyl and lower cycloalkenyl.

More preferably, $R^1$ is selected from phenyl, naphthyl, biphenyl, thienyl, pyridyl, thiazolyl, oxazolyl, imidazolyl, pyrazolyl, tert-butyl, ethenyl, 2-propenyl, 3-butenyl, propargyl, 1-cyclopentenyl, 1-cyclohexenyl, 1-cyclobutenyl and 1-cycloheptenyl; and $R^4$ is selected from hydrido, methyl, ethyl, propyl, isopropyl, butyl, iso-butyl, tert-butyl, pentyl, hexyl, phenyl, naphthyl, thienyl, pyridyl, thiazolyl, oxazolyl, imidazolyl, pyrazolyl, ethenyl, butenyl and propenyl; wherein any of the foregoing $R^1$ and $R^4$ groups are substituted at one or more substitutable positions with one or more radicals independently selected from fluoro, chloro, bromo, iodo, methoxy, ethoxy, propoxy, butoxy, pentoxy, methylenedioxy, methyl, ethyl, propyl, isopropyl, butyl, iso-butyl, tert-butyl, pentyl, hexyl, thienyl, pyridyl, thiazolyl, oxazolyl, imidazolyl, pyrazolyl, phenyl, cyclobutenyl, cyclopentenyl and cyclohexenyl.

Even more preferably, $R^1$ is selected from phenyl, thienyl, pyridyl and tert-butyl, wherein $R^1$ is optionally substituted at a substitutable position with one or more radicals selected from fluoro, chloro, bromo, iodo, thienyl, pyridyl, thiazolyl, oxazolyl, imidazolyl, pyrazolyl, phenyl and cyclopentenyl; and $R^4$ is selected from hydrido, methyl and phenyl.

The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, iso-butyl, sec-butyl, tert-butyl, pentyl, iso-amyl, hexyl and the like. Where the term "alkenyl" is used, it embraces linear or branched carbon-carbon double bond-containing radicals having two to about twenty carbon atoms or, preferably, two to about twelve carbon atoms. More preferred alkenyl radicals are "lower alkenyl" radicals having two to about six carbon atoms. Suitable "lower alkenyl" may be a straight or branched one such as vinyl, allyl, isopropenyl, propenyl, butenyl, pentenyl or the like. Where the term "alkynyl" is used, it embraces linear or branched carbon-carbon triple bond-containing radicals having two to about twenty carbon atoms or, preferably, two to about twelve carbon atoms. More preferred alkynyl radicals are "lower alkynyl" radicals having two to about six carbon atoms. Suitable "lower alkynyl" may be a straight or branched one such as ethynyl, propynyl, propargyl or the like. The term "halo" means halogens such as fluorine, chlorine, bromine or iodine. The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The "alkoxy" radical may be further substituted with one or more halo atoms, such as fluoro, chloro or bromo, to provide haloalkoxy radicals. Examples of such radicals include trifluoromethoxy and trifluoroethoxy. The term "cycloalkenyl" embraces unsaturated radicals having three to ten carbon atoms. More preferred cyclopentenyl radicals are "lower cyclopentenyls" having four to seven carbon atoms. Examples of such radicals include cylopropenyl, cyclobutenyl, cyclopentenyl, cyclohexenyl and cycloheptenyl. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The term "heteroaryl" embraces unsaturated heterocyclic radicals. Examples of "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino.

The term "alkylthio" embraces radicals containing a linear or branched alkyl radical, of one to about ten carbon atoms attached to a divalent sulfur atom, such as a methythio radical, ($CH_3$—S—). The term "alkylsulfinyl" embraces radicals containing a linear or branched alkyl radical, of one to ten carbon atoms, attached to a divalent sulfine [—S(=O)—] radical. The terms "sulfonyl" or "sulfone", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denotes $NH_2O_2S$—. The "sulfonamidyl" radicals may be further substituted with one or more halo atoms, such as fluoro, chloro or bromo, to provide haloalkylsulfonyl radicals, alkyl radicals, alkenyl radicals, aryl and heteroaryl radicals. The term "aminating agent" embraces compounds which add an amino radical onto the desired base group. Preferred aminating agents include haloamines, alkylhaloamines, alkenylhaloamines, heteroarylhaloamines and hydroxylamine-O-sulfonic acid. The term "silylalkylsulfone" embraces compounds with alkylsulfonyl radicals having a silyl ($R_3Si$—) group attached to the alkyl portion, which may increase the alkyl chain length on the sulfone. "Haloalkyltrialkylsilane" embraces reagents having haloalkyl radicals attached to a silyl group. More preferred are "lower haloalkyltrialkylsilanes" having alkyl portions of one to six carbons long. "Alkylammonium halides" embrace reagents having tetra(alkyl)ammonium halide salts. More preferred are "lower alkylammonium halides" having alkyl portions of one to six carbons long.

A general Scheme for the preparation of sulfonamides, useful as pharmaceutical agents and specifically as antiinflammatory agents, is shown in Scheme I below.

Scheme I

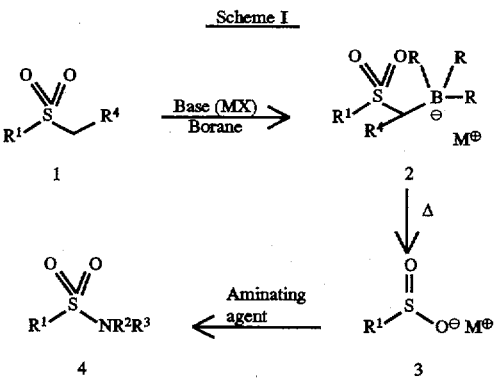

Synthetic Scheme I shows the three steps of the present method. In step one, deprotonation of sulfones 1 by treatment with a suitable base in a suitable solvent, at a temperature of about −70° C. to about 25° C., and treatment with an alkylborane gives an alkylborate.sulfone complex 2. In step two, heating the alkylborate.sulfone complex 2 at a temperature of about 20° C. to about 90° C. (reflux) converts the complex 2 into a sulfinic acid salt 3. In step three, treatment of the sulfinic acid salt 3 with an aminating agent at a temperature of about 0° C. to about 25° C. gives the desired sulfonamide 4. Alternatively, the solvent may be removed before the aminating agent is added.

Suitable bases for the deprotonation of sulfone 1 include alkyllithium reagents, lithioamides and Grignard reagents. Examples of such bases include n-butyllithium, methyllithium, lithium diisopropylamide (LDA), butylmagnesium chloride, phenylmagnesium bromide and methylmagnesium chloride. Methylmagnesium chloride is preferably used as the base.

A preferred method for deprotonating the sulfone 1 involves the addition of an excess of base to 1 mole of sulfone 1. More preferably, about 1 to about 1.5 moles of base are added and even more preferably, about 1.1 moles of base are added.

Suitable alkylboranes for the formation of alkylborate-.sulfone complex 2 include trialkylboranes. Examples of such trialkylboranes include trimethylborane, triethylborane, tributylborane and triallylborane. Triethylborane is preferably used as the alkylborane.

A preferred method for forming the alkylborate.sulfone complex 2 involves the addition of a molar excess of borane to sulfone 1. More preferably, about 1.25 to about 1.75 times molar excess is added, and even more preferably, about 1.5 times molar excess of borane is added.

The deprotonation of sulfone 1 and the formation of alkylborate.sulfone complex 2 are conveniently carried out in the temperature range of about −70° C. to about 25° C., preferably at about −20° C. to about 0° C.

The conversion of alkylborate.sulfone complex 2 into sulfinic acid salt 3 is carried out at a temperature of about 20° C. to about 90° C. (which may depend on the boiling point of the solvent).

Suitable solvents for the deprotonation of sulfone 1, the formation of alkylborate.sulfone complex 2 and the conversion into sulfinic acid salt 3 include organic solvents which are inert under the reaction conditions. Examples of such solvents include linear and cyclic ethers. Specifically, the solvent may be selected from tetrahydrofuran, dimethoxyethane and diethylether.

A dry inert atmosphere is preferable for the deprotonation of sulfone 1, the formation of alkylborate.sulfone complex 2 and the conversion into sulfinic acid salt 3.

The order of the addition of the base and the alkylborane is not critical, especially where the base is an alkyllithium reagent or a lithioamide. By adding the alkylborane first, the overall reaction may be in a more concentrated solution.

Aminating agents are those reagents which are capable of adding an amine, either substituted or primary, to the sulfinic acid salt 3. Suitable aminating agents for the treatment of the sulfinic acid salt 3 include haloamines, alkylhaloamines, alkenylhaloamines, heteroarylhaloamines, O-mesitylenesulfonylhydroxylamine and hydroxylamine-O-sulfonic acid. Examples of such aminating agents include those referenced by F. Scully, Jr. [J. Org. Chem., 46, 5077 (1981)], namely allyl-chloroamine, N-chloroamine, hexyl-chloroamine, butyl-chloroamine, diisobutyl-chloroamine, diethyl-chloroamine, dimethyl-chloroamine, N-chloropiperidine, N-chloropyrrolidine, N-chloromorpholine and N-chlorotetrahydroisoquinoline, O-mesitylenesulfonylhydroxylamine and hydroxylamine-O-sulfonic acid.

Where the aminating agent is hydroxylamine-O-sulfonic acid, the amination preferably takes place in the presence of aqueous base. Suitable aqueous bases include those capable of neutralizing the acid given off during the amination step and maintaining a slightly basic pH. Sodium acetate is preferred.

A preferred method for forming the sulfonamides 4 involves the addition of at least an equimolar amount of aminating agent to sulfinic acid salt 3. More preferably, about 10 to about 50 times molar excess is added, and even more preferably, about 35 times molar excess of aminating agent is added.

The amination is carried out at a temperature of about 0° C. to about 25° C., preferably at about 20° C. to about 25° C.

Preferably, the amination is carried out at basic pH. More preferably, the pH should be in a range of about 8–10.

Scheme II

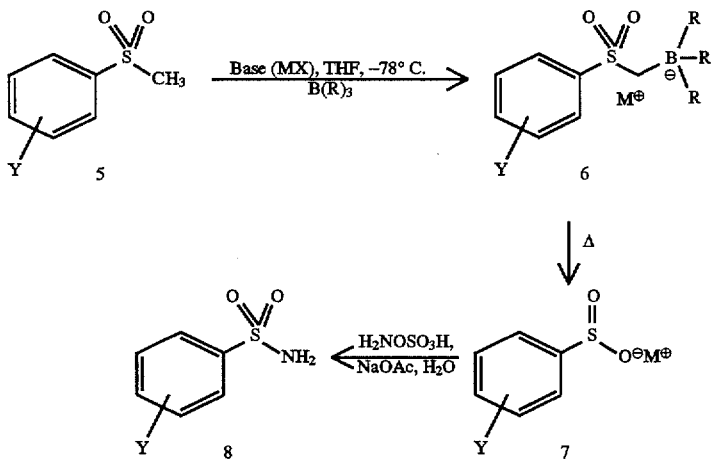

Specifically, Synthetic Scheme II shows the three step procedure used to prepare phenylsulfonamides 8, where Y is one or more radicals selected from halo, alkyl, alkoxy, heteroaryl, aryl and cycloalkyl, from the corresponding methylsulfones 5. In step one, the treatment of methylsulfones 5 with a suitable base at temperature of about −70° C. to about 20° C., and treatment with trialkylborane such as triethylborane or tributylborane in tetrahydrofuran gives the borane complexed derivative 6. In step two, the borane complexed derivative 6 is converted to the phenylsulfinic acid salt 7 by heating at a temperature of about 20° C. to about 90° C. for several hours (2 to 80 hours). The treatment of this phenylsulfinic acid salt 7 at about 0° C. to about 25° C. with aqueous sodium acetate followed by reaction with hydroxylamine-O-sulfonic acid gives desired sulfonamides 8 of this invention.

Suitable bases for the deprotonation of sulfone 5 include alkyllithium reagents, lithioamides and Grignard reagents. Examples of such bases include n-butyllithium, methyllithium, lithium diisopropylamide (LDA), butylmagnesium chloride, phenylmagnesium bromide and methylmagnesium chloride. Methylmagnesium chloride is preferably used as the base.

A preferred method for deprotonating the sulfone 5 involves the addition of an excess of base to 1 mole of sulfone 5. More preferably, about 1 to about 1.5 moles of base are added and even more preferably, about 1.1 moles of base are added.

Suitable alkylboranes for the formation of alkylborate.sulfone complex 6 include trialkylboranes. Examples of such trialkylboranes include trimethylborane, triethylborane, tributylborane and triallylborane. Triethylborane is preferably used as the alkylborane.

A preferred method for forming the alkylborate.sulfone complex 6 involves the addition of a molar excess of borane to sulfone 5. More preferably, about 1.25 to about 1.75 times molar excess is added, and even more preferably, about 1.5 times molar excess of borane is added.

The deprotonation of sulfone 5 and the formation of alkylborate.sulfone complex 6 are conveniently carried out in the temperature range of about −70° C. to about 25° C., preferably at about −20° C. to about 0° C.

The conversion of alkylborate.sulfone complex 6 into sulfinic acid salt 7 is carried out at a temperature of about 20° C. to about 90° C. (which may depend on the boiling point of the solvent).

Suitable solvents for the deprotonation of sulfone 5, the formation of alkylborate.sulfone complex 6 and the conversion into sulfinic acid salt 7 include organic solvents which are inert under the reaction conditions. Examples of such solvents include linear and cyclic ethers. Specifically, the solvent may be selected from tetrahydrofuran, dimethoxyethane and diethylether.

A dry inert atmosphere is preferable for the deprotonation of sulfone 5, the formation of alkylborate.sulfone complex 6 and the conversion into sulfinic acid salt 7.

Suitable aminating agents for the treatment of the sulfinic acid salt 7 include haloamines and hydroxylamine-O-sulfonic acid. Examples of such aminating agents include N-chloroamine, O-mesitylenesulfonylhydroxylamine and hydroxylamine-O-sulfonic acid.

Where the aminating agent is hydroxylamine-O-sulfonic acid, the amination preferably takes place in the presence of aqueous base. Suitable aqueous bases include those capable of neutralizing the acid given off during the amination step and maintaining a slightly basic pH. Sodium acetate is preferred.

A preferred method for forming the sulfonamides 8 involves the addition of at least an equimolar amount of aminating agent to sulfinic acid salt 7. More preferably, about 10 to about 50 times molar excess is added, and even more preferably, about 35 times molar excess of aminating agent is added. The amination is carried out at a temperature of about 0° C. to about 25° C., preferably at about 20° C. to about 25° C. Preferably, the amination is carried out at basic pH. More preferably, the pH should be in a range of about 8–10.

Scheme III

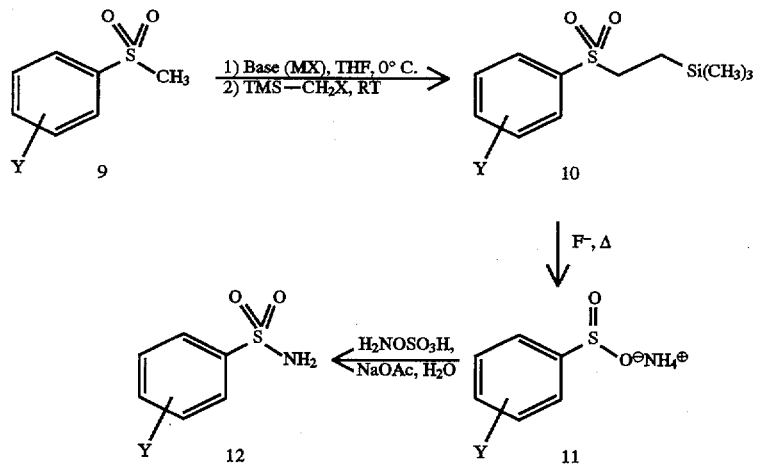

Specifically, Synthetic Scheme III shows the procedure used to prepare phenylsulfonamides 12, where Y is one or more radicals selected from halo, alkyl, alkoxy, heteroaryl, aryl and cycloalkyl, from the corresponding methylsulfones 9. In step one, the treatment of methylsulfones 9 with a suitable base at temperature of about −70° C. to about 20° C., and treatment with alkylsilanes, such as the haloalkyltrialkylsilanes (iodomethyl)trimethylsilane and (chloromethyl)trimethylsilane, at about 15° C. to about 30° C. in tetrahydrofuran gives the silylalkylsulfone 10. In step two, the silylalkylsulfone 10 is converted to the phenylsulfinic acid salt 11 by heating at a temperature of about 20° C. to about 90° C. with a silylalkyl-elimination agent, such as a fluoride ion. The treatment of this phenylsulfinic acid salt 7 as described above in Schemes I–II at about 0° C. to about 25° C. with aqueous sodium acetate followed by reaction with hydroxylamine-O-sulfonic acid gives desired sulfonamides 12 of this invention.

Suitable bases for the deprotonation of sulfone 9 include alkyllithium reagents, lithioamides and Grignard reagents. Examples of such bases include n-butyllithium, methyllithium, lithium diisopropylamide (LDA), butylmagnesium chloride, phenylmagnesium bromide and methylmagnesium chloride. Lithium diisopropylamide is preferably used as the base.

A preferred method for deprotonating the sulfone 9 involves the addition of an excess of base to 1 mole of sulfone 9. More preferably, about 1 to about 2 moles of base are added and even more preferably, about 1.2 moles of base are added.

Suitable alkylsilanes for the formation of the silylalkylsulfone 10 include haloalkyltrialkylsilanes. Examples of such haloalkyltrialkylsilanes include (iodomethyl)trimethylsilane and (chloromethyl)trimethylsilane.

A preferred method for forming the silylalkylsulfone 10 involves the addition of a molar excess of alkylsilane to sulfone 9. More preferably, about 1.5 to about 3 times molar excess is added, and even more preferably, about 2.0 times molar excess of silane is added.

The deprotonation of sulfone 9 is conveniently carried out in the temperature range of about −70° C. to about 25° C., preferably at about 0° C. The formation of silylalkylsulfone 10 is conveniently carried out in the temperature range of about 0° C. to about 35° C., preferably at about 20° C.

Suitable silylalkyl-elimination agents for the formation of the sulfinates include compounds which produce a fluoride ion. Examples of such compounds include alkylammonium fluorides and cesium fluoride. Tetrabutylammonium fluoride is preferred.

The conversion of silylalkylsulfone 10 into sulfinic acid salt 11 is carried out at a temperature of about 20° C. to about 90° C. (which may depend on the boiling point of the solvent).

Suitable solvents for the deprotonation of sulfone 9, the formation of silylalkylsulfone 10 and the conversion into sulfinic acid salt 11 include organic solvents which are inert under the reaction conditions. Examples of such solvents include linear and cyclic ethers. Specifically, the solvent may be selected from tetrahydrofuran, dimethoxyethane and diethylether.

A dry inert atmosphere is preferable for the deprotonation of sulfone 9, the formation of silylalkylsulfone 10 and the conversion into sulfinic acid salt 11.

Suitable aminating agents for the treatment of the sulfinic acid salt 11 include haloamines and hydroxylamine-O-sulfonic acid. Examples of such aminating agents include N-chloroamine, O-mesitylenesulfonylhydroxylamine and hydroxylamine-O-sulfonic acid.

Where the aminating agent is hydroxylamine-O-sulfonic acid, the amination preferably takes place in the presence of aqueous base. Suitable aqueous bases include those capable of neutralizing the acid given off during the amination step and maintaining a slightly basic pH. Sodium acetate is preferred.

A preferred method for forming the sulfonamides 12 involves the addition of at least an equimolar amount of aminating agent to sulfinic acid salt 11. More preferably, about 10 to about 50 times molar excess is added, and even more preferably, about 35 times molar excess of aminating agent is added. The amination is carried out at a temperature of about 0° C. to about 25° C., preferably at about 20° C. to about 25° C. Preferably, the amination is carried out at basic pH. More preferably, the pH should be in a range of about 8–10.

A further advantage of the present process is that materials can be carried through the above steps without purification of the intermediate compounds. However, if purification is desired, the intermediates disclosed can be isolated.

The following examples contain detailed descriptions of the methods of preparation of sulfonamides of Formula I. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

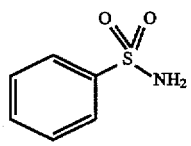

A solution of (phenylsulfonyl)methane (10 mmol) in 5 mL of THF at 0° C. was treated with 4.5 mL (12.6 mmol) of methylmagnesium chloride (2.8M in THF), and the resulting solution was stirred at room temperature for 30 minutes. The solution was cooled to 0° C., treated with 15 mL (15 mmol) of tributylborane (1M in THF), stirred at room temperature for 30 minutes, and then stirred at reflux for 18 hours. To the resulting mixture at 0° C. was added 5.7 g of sodium acetate, 25 mL of water, and 3.95 g of hydroxylamine-O-sulfonic acid; the resulting mixture was stirred at room temperature for 3 hours. The organic layer was diluted with ethyl acetate, washed with saturated $NaHCO_3$ and then brine, dried ($MgSO_4$), filtered, and concentrated in vacuo. Purification by silica gel chromatography gave 1.06 g (67%) of phenylsulfonamide.

The compounds of Example 1 and other compounds that can be formed with the method of the invention are listed in TABLE I. All new compounds were fully characterized spectrally and purity was established by combustion analysis (+0.4%). The relative amounts of unreacted starting sulfone and formed sulfonamide were analyzed by reverse phase HPLC on a $C_{18}$ column (Waters Delta Pak, 100A, 3.9 mm×30 cm), eluting with water and acetonitrile containing 0.05% trifluoroacetic acid, and detected by UV at 254 nm.

TABLE I

| Ex. | $R^1$ | Base | Borane | Sulfone[1] | Sulfonamide[1] |
|---|---|---|---|---|---|
| 1 | Phenyl | MeMgCl | $B(Bu)_3$ | 15 [2] | 67 [70] |
| 2 | Phenyl | MeMgCl | $B(Et)_3$ | 40 [50] | 50 [50] |
| 3 | Phenyl | LDA | $B(Et)_3$ | [26] | [58] |
| 4 | Phenyl | MeMgCl | $B(allyl)_3$ | [60] | [6] |
| 5 | Phenyl | MeMgCl | $B(Ph)_3$ | (100) | (0) |
| 6 | 4-Cl-Phenyl (r.t.) | MeMgCl | $B(Bu)_3$ | [60] | [15] |
| 7 | 4-Cl-Phenyl (reflux) | MeMgCl | $B(Bu)_3$ | 38 [20] | 36 [61] |
| 8 | 4-Br-Phenyl | MeMgCl | $B(Bu)_3$ | 20 [18] | 43 [60] |
| 9 | 4-MeO-Phenyl | MeMgCl | $B(Bu)_3$ | 28 [30] | 66 [66] |
| 10 | 2-Thienyl | MeMgCl | $B(Bu)_3$ | 32 (27) | 43 (46) |
| 11 | t-Butyl | MeMgCl | $B(Bu)_3$ | (58) | (42) |

[1]Isolated yields, [ ] indicates HPLC ratios and ( ) indicates $^1H$ NMR ratios.

EXAMPLE 12

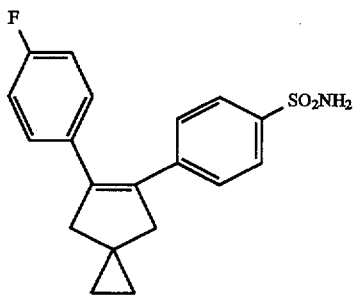

4-[6-(4-Fluorophenyl)spiro[2.4]hept-5-en-5-yl]
benzenesulfonamide

Step 1

Preparation of 4-(methylthio)acetophenone

To a stirred solution of 50 g (340 mmol) of 4-(methylthio) benzonitrile in 2 L of THF at −78° C. under an atmosphere of nitrogen was added 282 mL (390 mmol) of methyllithium (1.4M in diethyl ether) over a period of ten minutes. The solution was stirred at −78° C. for one hour, and then the dry ice bath was removed. After five hours, 100 mL of water followed by 200 mL of 3N hydrochloric acid were added to the reaction mixture and it was stirred overnight. Concentration in vacuo gave a residue which was partitioned between ethyl acetate and water. The water layer was extracted with three portions of ethyl acetate and the combined ethyl acetate layers were dried (MgSO$_4$). Concentration in vacuo gave 58 g of crude (4-methylthio) acetophenone as a solid: NMR (CDCl$_3$) δ 2.52 (s, 3H), 2.57 (s, 3H), 7.26 (d, J=9 Hz, 2H), 7.87 (d, J=9 Hz, 2H).

Step 2

Preparation of 4-(methylsulfonyl)acetophenone

To a solution of 11.73 g (71.1 mmol) of 4-(methylsulfonyl)acetophenone (prepared in Step 1) in 500 mL of dichloromethane at ambient temperature was added 61.14 g (177 mmol) of m-chloroperoxybenzoic acid (50%) (MCPBA) in portions over 20 minutes. The reaction was stirred for two hours, quenched slowly with aqueous sodium bisulfite, washed with three 100 mL portions of saturated sodium bicarbonate, dried (MgSO$_4$), and concentrated in vacuo to give 11.91 g (91%) of (4-methylsulfonyl) acetophenone as a colorless solid: NMR (CDCl$_3$) δ 2.67 (s, 3H), 3.08 (s, 3H), 8.06 (d, J=9 Hz, 2H), 8.14 (d, J=9 Hz, 2H).

Step 3

Preparation of 2-bromo-4'-(methylsulfonyl) acetophenone

To a stirred solution of 11.91 g (60.5 mmol) of 4-(methylsulfonyl)acetophenone (prepared in Step 2) in 133 mL of glacial acetic acid and 0.11 mL of hydrochloric acid at ambient temperature was added a solution of 8.22 g (51.4 mmol) of bromine in 9.3 mL of glacial acetic acid over a period of three hours. The reaction mixture was diluted with 500 mL of water and extracted with chloroform. The combined extracts were dried (MgSO$_4$) and concentrated in vacuo to give 15.7 g of crude 2-bromo-(4'-methylsulfonyl) acetophenone as a solid: NMR (CDCl$_3$) δ 3.10 (s, 3H), 4.45 (s, 2H), 8.08 (d, J=9 Hz, 2H), 8.17 (d, J=9 Hz, 2H).

Step 4

Preparation of 2-(4-fluorophenyl)-1-[2-[4-(methylsulfonyl)phenyl]-2-oxoethoxy]ethanone To a stirred solution of 4.45 g (28.9 mmol) of 4-fluorophenylacetic acid in 3.26 g (31.8 mmol) of triethylamine and 275 mL of acetonitrile was added 8.9 g (28.9 mmol) of 2-bromo-4'-(methylsulfonyl)acetophenone (prepared in Step 3) at ambient temperature. The reaction mixture was stirred for 30 minutes, concentrated in vacuo, and partitioned between ethyl acetate and water. The organic phase was dried MgSO$_4$) and concentrated in vacuo. Purification by silica gel chromatography with ethyl acetate/ hexane (1:1) gave 6.87 g (68%) of 2-(4-fluorophenyl)-1-[2-[4-(methylsulfonyl)phenyl]-2-oxoethoxy]ethanone as a colorless solid: NMR (CDCl$_3$) δ 3.08 (s, 3H), 3.79 (s, 2H), 5.35 (s, 2H), 7.06 (s, t, J=9 Hz, 2H), 7.32 (dd, J=6 and 9 Hz, 2H), 8.06 (s, 4H).

Step 5

Preparation of 3-(4-fluorophenyl)-4-[(4-methylsulfonyl)phenyl]-5H-furan-2-one

Under nitrogen, 4.10 g (11.7 mmol) of 2-(4-fluorophenyl) -1-[2-[4-(methylsulfonyl)phenyl]-2-oxoethoxy]ethanone (prepared in Step 4), 6.52 mL (46.8 mmol) of triethylamine, 4.89 g (25.7 mmol) of p-toluenesulfonic acid, and 12 g of 4 Å molecular sieves were added to 117 mL of acetonitrile and stirred at reflux for 16 hours. The reaction mixture was concentrated in vacuo and the residue partitioned between dichloromethane and water. The dichloromethane layer was dried (MgSO$_4$) and reconcentrated in vacuo. Recrystallization from hexane/ethyl acetate (2:1) gave 3.65 g (94%) of 3-(4-fluorophenyl)-4-[(4-methylsulfonyl)phenyl]-5H-furan-2-one as a solid: mp 166°–167° C.; NMR (CDCl$_3$) δ 3.08 (s, 3H), 5.19 (s, 2H), 7.10 (t, J=9 Hz, 2H), 7.42 (dd, J=6 and 9 Hz, 2H), 7.52 (d, J=9 Hz, 2H), 7.97 (d, J=9 Hz, 2H). HRMS. Calc'd for C$_{17}$H$_{13}$FO$_4$S: 332.0519. Found: 332.0501. Anal. Calc'd for C$_{17}$H$_{13}$FO$_4$S: C, 61.44; H, 3.94; O, 19.26. Found: C, 61.11; H, 4.06; O, 19.32.

Step 6

Preparation of 2-(4-fluorophenyl)-3-[(4-methylsulfonyl)phenyl]-1,4-dihydroxy-2-butene To a solution of 3.08 g (9.28 mmol) of 3-(4-fluorophenyl) -4-[(4-methylsulfonyl)phenyl]-5H-furan-2-one (prepared in Step 5) in 93 mL of tetrahydrofuran (THF) at −78° C. under an atmosphere of nitrogen was added 20 mL (30 mmol) of diisobutylaluminum hydride (DIBAL) (1.5M in THF) over a 10 minute period. The solution was stirred at −78° C. for 20 minutes, allowed to warm to ambient temperature, and stirred overnight. An additional 15 mL (22 mmol) aliquot of DIBAL was added and stirring was continued for 2 hours. The reaction was cooled to −78° C., treated dropwise with 25 mL of acetone, warmed to room temperature, and slowly treated with 25 mL of water. The mixture was stirred for 30 minutes prior to the careful addition of 35 mL of 1.2N sodium hydroxide. The mixture was extracted with ethyl acetate, washed with 1N hydrochloric acid followed by brine, dried (MgSO$_4$), and concentrated in vacuo to give 3.8 g of crude 2-(4-fluorophenyl)-3-[(4-methylsulfonyl)phenyl] -1,4-dihydroxy-2-butene as a colorless oil: NMR (CDCl$_3$) δ 2.98 (s, 3H), 4.60 (d, J=6 Hz, 4H), 6.8 (t, J=9 Hz, 2H), 6.94–7.02 (m, 2H), 7.22 (d, J=9 Hz, 2H), 7.65 (d, J=9 Hz, 2H).

Step 7

Preparation of 2-(4-fluorophenyl)-3-[(4-methylsulfonyl)phenyl]-1,4-dichloro-2-butene To a solution of 3.5 g (7.62 mmol) of crude 2-(4-fluorophenyl)-3-[(4-methylsulfonyl)phenyl]-1,4-dihydroxy-2-butene (prepared in Step 6) in 58 mL of N,N-dimethylformamide (DMF) at 5° C. under an atmosphere of nitrogen was added dropwise 1.52 mL (20.84 mmol) of thionyl chloride. The reaction was stirred at 5° C. for 22 hours, stirred at ambient temperature for an additional 8 hours, and concentrated in vacuo. The residue was partitioned between ethyl acetate and water; the ethyl acetate phase was dried (MgSO$_4$) and concentrated in vacuo to give crude 2-(4-fluorophenyl)-3-[(4-methylsulfonyl)phenyl]-1,4-dichloro-2-butene as a solid: NMR (CDCl$_3$) δ 3.0 (s, 3H), 4.55 (d, J=3.4 Hz, 4H), 6.86 (t, J=9 Hz, 2H), 6.75 (d, J=8.3 Hz, 2H), 7.45 (d, J=9 Hz, 2H).

Step 8, A

Preparation of 1-[2-(4-fluorophenyl)-4,4-dicarbomethoxycyclopenten-1-yl]-4-(methylsulfonyl)benzene To a solution of 1.2 mL (10.5 mmol) of dimethyl malonate in 10 mL of DMF under an atmosphere of nitrogen was added 215 mg (26.9 mmol) of lithium hydride in portions. The resulting suspension was stirred at ambient temperature for 20 minutes prior to the addition of a solution of crude 2-(4-fluorophenyl)-3-[(4-methylsulfonyl)phenyl]-1,4-dichloro-2-butene (prepared in Step 7) in 10 mL of DMF. The reaction was stirred at ambient temperature for 15 hours, treated with another 150 mg (18.8 mmol) of lithium hydride, and stirred for another 4 hours. The mixture was concentrated in vacuo and partitioned between ethyl acetate and water; the organic phase was dried (MgSO$_4$), and concentrated in vacuo. The residue was chromatographed on silica gel to give 1.1 g (34%) of 1-[2-(4-fluorophenyl)-4,4-dicarbomethoxycyclopenten-1-yl]-4-(methylsulfonyl)benzene as an oil: NMR (CDCl$_3$) δ 3.03 (s, 3H), 3.55 (s, 4H), 3.79 (s, 6H), 6.93 (t, J=9 Hz, 2H), 7.11 (dd, J=6 and 9 Hz, 2H), 7.32 (d, J=9 Hz, 2H), 7.77 (d, J=9 Hz, 2H).

Step 8, B

Preparation of 1-[2-(4-fluorophenyl)-4,4-dicarbomethoxycyclopenten-1-yl]-4-(methylsulfonyl)benzene To a solution of 7.18 mL (63 mmol) of dimethyl malonate in 160 mL of DMF at 0° C. under an atmosphere of nitrogen was added 3.0 g (75 mmol) of sodium hydride (60% suspension in oil). The reaction was stirred at ambient temperature for 15 minutes (or until the gas evolution has ceased), cooled to −20° C., and treated with 15 g (69 mmol) of 2-bromo-4'-fluoroacetophenone (Aldrich) in one portion. The mixture was stirred at ambient temperature for 1 hour and then cooled to 0° C.; another 75 mmol of sodium hydride was added and the resulting mixture stirred at ambient temperature for 15 minutes (or until the gas evolution has ceased). The reaction was recooled to −20° C. and treated with 19.1 g (69 mmol) of 2-bromo-4'-(methylsulfonyl)acetophenone (prepared in Step 3). The reaction was stirred at room temperature for 2 hours and concentrated in vacuo. The residue was partitioned between water and ethyl acetate; the ethyl acetate phase was dried (MgSO$_4$) and reconcentrated in vacuo. The residue was chromatographed on silica gel to give 13.8 g (51%) of dimethyl 2-[2-(4-fluorophenyl)-2-oxoethyl]-2-[2-[4-(methylsulfonyl)phenyl]-2-oxoethyl]propanedioate as an oil: NMR (CDCl$_3$) δ 3.06 (s, 3H), 3.76 (s, 6H), 4.03 (s, 2H), 4.08 (s, 2H), 7.13 (t, J=8.6 Hz, 2H), 7.97–8.05 [m with d at 8.03 (J=8.7 Hz), 4H], 8.14 (d, J=8.5 Hz, 2H).

To a vigorously stirred mixture of 50.4 g (771 mmol) of zinc dust in 640 mL of THF at −78° C. under an atmosphere of nitrogen was added dropwise 60.4 mL (551 mmol) of titanium(IV) chloride. The reaction was warmed to ambient temperature with a water bath and then stirred at reflux for 1 hour. To the resulting dark mixture under reflux was added a solution of 15 g (32.3 mmol) of dimethyl 2-[2-(4-fluorophenyl)-2-oxoethyl]-2-[2-[4-(methylsulfonyl)phenyl]-2-oxoethyl]propanedioate (prepared above) in 20 mL of THF. The resulting mixture was stirred at ambient temperature for 16 hours, filtered through a pad of Celite, rinsed with ethyl acetate, and concentrated in vacuo. The residue was partitioned between water and ethyl acetate; the organic phase was washed with brine, dried MgSO$_4$), and concentrated in vacuo. The residue was chromatographed on silica gel to give 6.26 g (44%) of 1-[2-(4-fluorophenyl)-4,4-dicarbomethoxycyclopenten-1-yl]-4-(methylsulfonyl)benzene which was identical to the material prepared in Step 8, Method A.

Step 9

Preparation of 1-[2-(4-fluorophenyl)-4,4-di(hydroxymethyl)cyclopenten-1-yl]-4-(methylsulfonyl)benzene Under nitrogen, a solution of 1.01 g (2.34 mmol) of 1-[2-(4-fluorophenyl)-4,4-dicarbomethoxycyclopenten-1-yl]-4-(methylsulfonyl)benzene (prepared in Step 8) in 1.5 mL of THF at −78° C. was treated with 11.6 mL (11.6 mmol) of DIBAL (1.0M in THF). The reaction was stirred at ambient temperature for 1.5 hours, quenched with acetone and aqueous NaOH, extracted with ethyl acetate, dried MgSO$_4$), and concentrated in vacuo to give 840 mg of crude 1-[2-(4-fluorophenyl)-4,4-di(hydroxymethyl)cyclopenten-1-yl]-4-(methylsulfonyl)benzene as a colorless oil: NMR (CDCl$_3$) δ 2.82 (d, J=5 Hz, 4H), 3.04 (s, 3H), 3.86 (d, J=5 Hz, 4H), 6.94 (t, J=9 Hz, 2H), 7.11 (dd, J=5 and 9 Hz, 2H), 7.33 (d, J=9 Hz, 2H), 7.77 (d, J=9 Hz, 2H).

Step 10

Preparation of 1-[2-(4-fluorophenyl)-4,4-di(tosylmethyl)cyclopenten-1-yl]-4-(methylsulfonyl)benzene Under nitrogen, a solution of 2.34 mmol of the crude 1-[2-(4-fluorophenyl)-4,4-di(hydroxymethyl)cyclopenten-1-yl]-4-(methylsulfonyl)benzene (prepared in Step 9) in 8 mL of pyridine at ambient temperature was treated with 1.2 g (6.3 mmol) of p-toluenesulfonyl chloride (tosyl chloride). The resulting solution was stirred at room temperature for 17 hours, concentrated in vacuo, and chromatographed on silica gel to give 1.06 g (66% overall yield from Step 9) of 1-[2-(4-fluorophenyl)-4,4-di(tosylmethyl)cyclopenten-1-yl]-4-(methylsulfonyl)benzene as a colorless solid: NMR (CDCl$_3$) δ 2.46 (s, 6H), 2.73 (s, 3H), 3.04 (s, 3H), 4.05 (s, 4H), 6.85–7.0 (m, 4H), 7.20 (d, J=8 Hz, 2H), 7.34 (d, J=8 Hz, 4H), 7.75 (d, J=8 Hz, 6H).

Step 11

Preparation of 5-(4-fluorophenyl)-6-[4-(methylsulfonylphenyl]spiro[2,4]hept-5-ene Under nitrogen, a solution of 1.02 g (1.49 mmol) of 1-[2-(4-fluorophenyl)-4,4-di(tosylmethyl)cyclopenten-1-yl]

-4-(methylsulfonyl)benzene (prepared in Step 10) in 24 mL of DMF was treated with 3.23 g (21.55 mmol) of sodium iodide and 1.61 g (24.63 mmol) of zinc dust. The reaction was stirred at 150° C. for 1.5 hour, concentrated in vacuo, and partitioned between water and ethyl acetate. The organic phase was washed with sodium sulfite, water, brine, dried (MgSO$_4$), and concentrated in vacuo. The residue was chromatographed on silica gel to give 437 mg (86%) of 5-(4-fluorophenyl)-6-[4-(methylsulfonyl)phenyl]spiro[2.4]hept-5-ene as a colorless solid: mp 140.5°–142.0° C.; NMR (CDCl$_3$) δ 0.69 (s, 4H), 2.92 (s, 4H), 3.04 (s, 3H), 6.93 (t, J=9 Hz, 2H), 7.10 (dd, J=5 and 9 Hz, 2H), 7.32 (d, J=8 Hz, 2H), 7.76 (d, J=8 Hz, 2H). HRMS. Calc'd for C$_{20}$H$_{19}$FO$_2$S: 342.1090. Found: 342.1126. Anal. Calc'd for C$_{20}$H$_{19}$FO$_2$S: C, 70.15; H, 5.59; F, 5.55; S, 9.36. Found: C, 70.10; H, 5.69; F, 5.50; S, 9.60.

Step 12

Preparation of 4-[6-(4-fluorophenyl)spiro[2,4]hept-5-en-5-yl]benzenesulfonamide

Under nitrogen, a solution of 90 mg (0.248 mmol) of 5-(4-fluoro phenyl)-6-[4-(methylsulfonyl)phenyl]spiro[2.4]hept-5-ene from step 11 in 1 mL of THF at −78° C. was treated with 0.21 mL (0.27 mmol) of methyllithium (1.3M in ether) over a period of 2 minutes. The reaction was stirred at ambient temperature for 25 minutes, cooled to −78° C., and treated with 0.3 mL (0.3 mmol) of tributylborane (1.0M in THF). The resulting dark brown solution was stirred at ambient temperature for 20 minutes and then at reflux for 16 hour prior to the addition of 350 mg (4.27 mmol) of sodium acetate, 2 mL of water, and 250 mg (2.21 mmol) of hydroxylamine-O-sulfonic acid. The resulting light orange mixture was stirred at ambient temperature for 3 hours and the aqueous phase extracted with ethyl acetate. The combined extracts were washed with water, brine, dried (MgSO$_4$), and concentrated in vacuo. The residue was chromatographed on silica gel to give 24 mg (27%) of 4-[6-(4-fluorophenyl)spiro[2.4]hept-5-en-5-yl]benzenesulfonamide as a colorless solid: mp 131.0°–133.0° C.; NMR (CDCl$_3$) δ 0.68 (s, 4H), 2.90 (s, 3H), 4.81 (s, 2H), 6.92 (t, J=9 Hz, 2H), 7.11 (dd, J=6 and 9 Hz, 2H), 7.27 (d, J=9 Hz, 2H), 7.74 (d, J=9 Hz, 2H). HRMS. Calc'd for C$_{19}$H$_{18}$FNO$_2$S: 344.1121. Found: 344.1122. Anal. Calc'd for [C$_{19}$H$_{18}$FNO$_2$S+0.1 CH$_3$CO$_2$CH$_2$CH$_3$]: C, 66.16; H, 3.98; S, 9.11. Found: C, 65.86; H, 5.52; N, 3.92; S, 9.57.

EXAMPLE 13

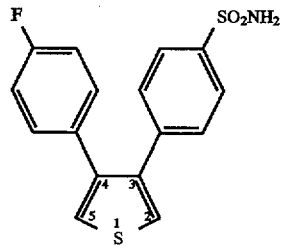

4-[4-(4-Fluorophenyl)thien-3-yl]benzenesulfonamide

Step 1

Preparation of dimethyl thiodiglycolate

A 2 L, 4-neck round bottom flask equipped with a mechanical stirrer was charged with thiodiglycolic acid (300.3 g, 2 mol) and methanol (810 ml). Anhydrous HCl was then bubbled through this solution with stirring for 0.5 hours. Stirring was continued for an additional 16 hours at 27° C. at which time the methanol was removed by distillation at reduced pressure. The residue was dissolved in diethyl ether and washed with brine (300 ml), twice with saturated bicarbonate (2×500 ml) and brine (500 ml). The diethyl ether was dried with Na$_2$SO$_4$ and the solvent removed by distillation at reduced pressure. Vacuum distillation of the resulting residue yielded 229.7 g (1.29 mol, 64%) of dimethyl thiodiglycolate; $^1$H NMR (CDCl$_3$) δ 3.37 (s, 4H), 3.72 (s, 6H).

Step 2

Preparation of 2-methoxycarbonyl-3-(4'-fluorophenyl)-4-(4'-methylthiophenyl)-thienyl-5-carboxylic acid and 2-methoxycarbonyl-3-(4'-methylthiophenyl)-4-(4'-fluorophenyl)-thienyl-5-carboxylic acid To a stirred solution of 4-fluoro-4'-methylthio benzil (33.34 g, 122 mmol) and dimethyl thiodiglycolate (43.4 g, 244 mmol) from Step 1 in tetrahydrofuran (THF) (400 ml) at ambient temperature was added 25% NaOMe in methanol solution (83.7 ml, 366 mmol). This solution was immediately warmed to 65° C. and stirred for 2.5 hours. The reaction mixture was cooled to room temperature and poured into 1 L of 2M NH$_4$OH and 1 L diethyl ether, shaken, and separated. The aqueous layer was acidified with concentrated HCl, saturated with NaCl, and extracted with 1 L ethyl acetate. The ethyl acetate was dried over Na$_2$SO$_4$ and concentrated in vacuo to provide 73.43 g of crude intermediate as a tan solid. The crude intermediate was recrystalized from ethyl acetate/iso-octane to provide 39 g (82%) of 2-methoxycarbonyl-3-(4'-fluorophenyl)-4-(4'-methylthiophenyl)-thienyl-5-carboxylic acid as a white crystalline solid.

Step 3

Preparation of 3-(4'-methylthiophenyl)-4-(4'-fluorophenyl)-thienyl-2,5-dicarboxylic acid.

To a solution of 2-methoxycarbonyl-3-(4'-fluorophenyl)-4-(4'-methylthiophenyl)-thienyl-5-carboxylic acid (39 g, 93.6 mmol) from Step 2 in 450 ml THF was added 1N NaOH (468 ml). Enough methanol was added to bring reagents back into solution (~75 ml). The reaction was then heated to reflux for 1.5 hours at which time the reaction was determined to be complete by HPLC monitoring. The reaction mixture was washed with diethyl ether (500 ml), acidified with conc. HCl, saturated with NaCl, and extracted twice with 500 ml ethyl acetate. The ethyl acetate was dried over MgSO$_4$ and concentrated in vacuo to yield 36.84 g of 3-(4'-methylthiophenyl)-4-(4'-fluorophenyl)-thienyl-2,5-dicarboxylic acid.

Step 4

Preparation of 3-(4'-methylthiophenyl)-4-(4'-fluorophenyl)thiophene

The diacid from Step 3 (36.84 g, 94.9 mmol) was suspended in 400 ml of freshly distilled quinoline and heated to 180°–200° C. in an oil bath at which time copper powder (3.6 g) was added in one portion. The reaction was stirred at 180°–200° C. for 3 hours, cooled to 130° C., filtered through a medium frit glass funnel then cooled to room temperature.

The quinoline was acidified with 3N HCl and extracted twice with diethyl ether (400 ml). The diethyl ether was dried and concentrated to provide 27.83 g of a dark brown solid. The brown solid was dissolved in a minimum amount of ethyl acetate and passed over silica in hexane. The silica was washed with 50% ethyl acetate in hexane until no further product eluted. The product containing fractions were combined and concentrated to provide 25.37 g (89%) of 3-(4'-methylthiophenyl)-4-(4'-fluorophenyl)-thiophene as a white solid.

Step 5

Preparation of 3-(4-methylsulfonylphenyl)-4-(4-fluorophenyl)thiophene 3-(4'-methylthiophenyl)-4-(4'-fluorophenyl)thiophene (21.3 g, 70.9 mmol) from Step 4 was dissolved in 500 ml dichloromethane and cooled to –78° C. To this solution was added 50–60% 3-chloroperoxybenzoic acid (MCPBA) (44.5 g, 142 mmol). The reaction was stirred at –78° C. for 1.5 hours at which time the cooling bath was replaced with an ice bath and the reaction stirred at 0° C. until reaction was complete by monitoring with HPLC. The reaction was warmed to room temperature, washed with 1M NaHSO₃ solution (500 ml), saturated NaHCO₃ (500 ml) and brine. The reaction solution was dried over Na₂SO₄ and concentrated in vacuo. This material was dissolved in 250 ml dichloromethane and 350 ml absolute ethanol was added. The dichloromethane was removed by boiling and the solution cooled to 10° C. for a few hours. 3-(4-Methylsulfonylphenyl)-4-(4-fluorophenyl)-thiophene (16 g) was collected by filtration on a medium frit funnel. Melting point 190.5°–191.5° C.

Step 6

Preparation of 4-[4-(4-fluorophenyl)thien-3-yl] benzenesulfonamide

To a solution of 3-(4-methylsulfonylphenyl)-4-(4-fluorophenyl)thiophene (0.332 g, 1.0 mmol) from Step 5 in THF (8 mL) at –70° C. under nitrogen was added 1.6M n-butyllithium in hexane (0.66 mL, 1.05 mmol) slowly, via syringe, and the mixture stirred at –70° C. for 20 minutes and then at room temperature (25° C.) for 1 hour. After cooling to –70° C., a 1.0M solution of tri-n-butyl borane in THF (1.15 mL, 1.15 mmol) was added and the mixture allowed to warm slowly to 0° C. for 1 hour, warmed to room temperature for 2 hours, and finally stirred at reflux overnight (18 hours). After cooling to room temperature and stirring for 3 hours, water (0.8 mL) was added followed by sodium acetate (0.6 g) and hydroxylamine-O-sulfonic acid (0.41 g). After stirring at room temperature overnight, the mixture was poured into 3 volumes of ethyl acetate, and the organic layer washed with water and brine and dried over MgSO₄. After solvent removal, the white solids (a mixture of product and starting material) were separated via flash chromatography on silica gel using a 15% ethyl acetate/85% toluene eluant to yield 4-[4-(4-fluorophenyl)thien-3-yl] benzenesulfonamide as a white solid (59 mg, mp 194°–195° C.). Anal. Calc'd for C₁₆H₁₂NO₂S₂F: C, 57.64; H, 3.63; N, 4.20. Found: C, 57.37; H, 3.69; N, 3.99.

EXAMPLE 14

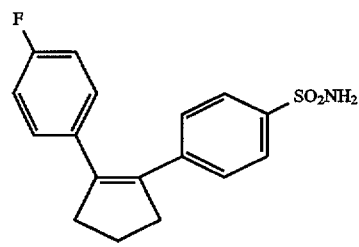

4-[2-(4-Fluorophenyl)cyclopenten-1-yl] benzenesulfonamide n-Butyllithium (0.54 mL, 1.34 mmol, 2.49M) was added dropwise via syringe to 1-[2-(4-fluorophenyl)cyclopenten-1-yl]-4-(methylsulfonyl)benzene (prepared as described in U.S. Pat. No. 5,344,991) (0.352 g, 1.11 mmol) and dry tetrahydrofuran (THF) (3.5 mL) cooled in an ice-bath. The resulting orange solution was stirred for 1 hour in the ice-bath and (chloromethyl)trimethylsilane (235 μL, 1.68 mmol) was added in one portion via syringe. The ice-bath was removed and the reaction mixture was stirred for 6 hours at room temperature. Tetrabutylammonium fluoride (6.0 mL, 6.00 mmol, 1M in THF) was added in one portion via syringe, and the resulting mixture was heated to reflux for 45 minutes, then cooled to room temperature. To the reaction mixture was added sequentially NaOAc (0.501 g, 6.11 mmol), water (15.0 mL), and H₂NOSO₃H (0.712 g, 6.30 mmol) and the reaction was stirred overnight at room temperature. The reaction mixture was diluted with ethyl acetate (20.0 mL), the layers were separated, and the organic layer was washed with saturated NaHCO₃ (2× 10 mL), water (10.0 mL), and brine (10.0 mL) then dried over MgSO₄. The solution was filtered, the solvents removed under reduced pressure, the crude product was purified by silica gel chromatography to afford 0.294 g (84%) of product as a white solid.

EXAMPLE 15

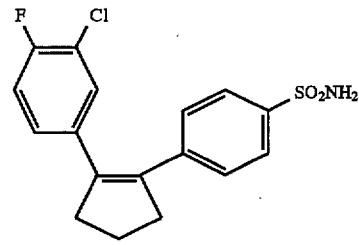

4-[2-(3-Chloro-4-fluorophenyl)cyclopenten-1-yl] benzenesulfonamide

Step 1

Alkylation of 1-[2-(3-chloro-4-fluorophenyl) cyclopenten-1-yl]-4-(methylsulfonyl)benzene Lithium diisopropylamide (LDA) (0.33 mL, 0.66 mmol, 2.00M) was added dropwise via syringe to 1-[2-(3-chloro-4-fluorophenyl)cyclopenten-1-yl]-4-(methylsulfonyl) benzene (prepared as in WO95/11883) (0.109 g, 0.31 mmol) and dry THF (0.5 mL) cooled in a dry-ice/isopropanol-bath. The resulting solution was stirred for 30 minutes in the dry-ice/isopropanol-bath and (iodomethyl)trimethylsilane (115 μL, 0.76 mmol) was added in one portion via syringe. The reaction mixture was stirred for 4 hours while slowly warming to room temperature, then quenched with 5% wt HCl. The mixture was diluted with ethyl acetate (10 mL), the layers were separated, and the organic layer was washed with water (5.0 mL) and brine (5.0 mL) and dried over $MgSO_4$. The solution was filtered and the solvents were removed under reduced pressure. The crude silane was purified by silica gel chromatography.

Step 2

Preparation of 4-[2-(3-chloro-4-fluorophenyl) cyclopenten-1-yl]benzenesulfonamide Tetrabutylammonium fluoride (0.83 mL, 0.83 mmol, 1M in THF) was added to the silane from Step 1 (0.121 g, 0.277 mmol) and dry THF (0.5 mL). The resulting mixture was refluxed for 1 hour then cooled to room temperature. To the reaction mixture was added sequentially NaOAc (0.103 g, 1.26 mmol), water (1.5 mL), and $H_2NOSO_3H$ (0.157 g, 1.38 mmol) and the reaction was stirred for 1 hour at room temperature. The reaction mixture was diluted with ethyl acetate (5.0 mL) and water (5.0 mL). The layers were separated, and the organic layer was washed with saturated $NaHCO_3$ (5.0 mL), water (5.0 mL), and brine (5.0 mL) then dried over $MgSO_4$. The solution was filtered, the solids washed with ethyl acetate, and the solvents removed under reduced pressure. The crude product was purified by silica gel chromatography to afford 0.087 g (97%) of product as a white solid.

From the foregoing detailed description, one skilled in the art can easily ascertain the essential characteristics of this invention, and without departing from the spirit and scope thereof, can make various changes and modifications of the invention to adapt it to various usages and conditions.

What is claimed is:

1. A method of preparing sulfonamides comprising the steps of forming a sulfinic acid salt from a sulfone, and treating said sulfinic acid salt with an aminating agent to form the sulfonamide.

2. A method of preparing sulfonamides of Formula I

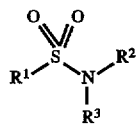

wherein $R^1$ is a radical not attached to the sulfur atom through a methylene radical; and wherein $R^2$ and $R^3$ are independently selected from hydrido, alkyl, alkenyl, aryl and heteroaryl, wherein the aryl and heteroaryl radicals are optionally substituted at a substitutable position with one or more radicals selected from halo, alkyl and alkoxy;

said method comprising the steps of converting a sulfone into a sulfinic acid salt, and forming the sulfonamide by treating said sulfinic acid salt with an aminating agent.

3. Method of claim 2 wherein the sulfone is converted into a sulfinic acid salt by forming a trialkylborate-sulfone complex by treating the sulfone with a base and an alkylborane, and converting the complex into said sulfinic acid salt.

4. Method of claim 3 wherein the base is selected from lithioamides, alkyllithiums and Grignard reagents.

5. Method of claim 4 wherein the base is selected from n-butyllithium, methyllithium, lithium diisopropylamide, methylmagnesium chloride, butylmagnesium chloride and phenylmagnesium bromide.

6. Method of claim 2 wherein $R^1$ is selected from aryl, heteroaryl, alkyl, alkenyl, alkynyl and cycloalkenyl, wherein $R^1$ is optionally substituted at a substitutable position with one or more radicals selected from halo, alkyl, alkoxy, heteroaryl, aryl and cycloalkenyl.

7. Method of claim 6 wherein $R^1$ is selected from phenyl, naphthyl, biphenyl, heteroaryl, lower alkyl, lower alkenyl, lower alkynyl and lower cycloalkenyl, wherein $R^1$ is optionally substituted at a substitutable position with one or more radicals selected from halo, lower alkyl, lower alkoxy, heteroaryl, phenyl, naphthyl, biphenyl and lower cycloalkenyl; and wherein $R^2$ and $R^3$ are independently selected from hydrido, lower alkyl, lower alkenyl, phenyl optionally substituted at a substitutable position with one or more radicals selected from halo, lower alkyl and lower alkoxy, and five or six membered heteroaryl optionally substituted at a substitutable position with one or more radicals selected from halo, lower alkyl and lower alkoxy.

8. Method of claim 7 wherein $R^1$ is selected from phenyl, naphthyl, biphenyl, thienyl, pyridyl, thiazolyl, oxazolyl, imidazolyl, pyrazolyl, tert-butyl, ethenyl, 2-propenyl, 3-butenyl, propargyl, 1-cyclopentenyl, 1-cyclohexenyl, 1-cyclobutenyl and 1-cycloheptenyl, wherein $R^1$ is optionally substituted at a substitutable position with one or more radicals selected from fluoro, chloro, bromo, iodo, methoxy, ethoxy, propoxy, butoxy, pentoxy, methylenedioxy, methyl, ethyl, propyl, isopropyl, butyl, iso-butyl, tert-butyl, pentyl, hexyl, thienyl, pyridyl, thiazolyl, oxazolyl, imidazolyl, pyrazolyl, phenyl, naphthyl, cyclobutenyl, cyclopentenyl and cyclohexenyl; and wherein $R^2$ and $R^3$ are independently selected from hydrido, methyl, ethyl, propyl, isopropyl, butyl, iso-butyl, tert-butyl, pentyl, hexyl, ethenyl, propenyl, isopropenyl, butenyl, iso-butenyl, allyl, pentenyl, phenyl and five or six membered heteroaryl selected from thienyl, pyridyl, thiazolyl, oxazolyl, imidazolyl, pyrazolyl, piperidinyl, pyrrolidinyl, morpholinyl and tetrahydroisoquinolinyl, wherein the heteroaryl and phenyl radicals are optionally substituted at a substitutable position with one or more radicals selected from fluoro, chloro, bromo, iodo, methyl, ethyl, propyl, isopropyl, butyl, isobutyl, tert-butyl, pentyl, hexyl, methoxy, ethoxy, propoxy, butoxy, pentoxy and methylenedioxy.

9. Method of claim 3 wherein the alkylborane is a trialkylborane.

10. Method of claim 9 wherein the alkylborane is selected from trimethylborane, triethylborane, tributylborane and triallylborane.

11. Method of claim 2 wherein the sulfone is converted into a sulfinic acid salt by silylalkylating the sulfone with a base and an alkylsilane to form the silylalkylsulfone, and treating the silylalkylsulfone with a silylalkyl-elimination agent to form said sulfinic acid salt.

12. Method of claim 11 wherein the base is selected from lithioamides, alkyllithiums and Grignard reagents.

13. Method of claim 12 wherein the base is selected from n-butyllithium, methyllithium, lithium diisopropylamide, methylmagnesium chloride, butylmagnesium chloride and phenylmagnesium bromide.

14. Method of claim 11 wherein the alkylsilane is a haloalkyltrialkylsilane selected from (iodomethyl) trimethylsilane and (chloromethyl)trimethylsilane.

15. Method of claim 11 wherein the silylalkyl-elimination agent is selected from alkylammonium fluorides and cesium fluoride.

16. Method of claim 15 wherein the alkylammonium fluoride is selected from tetrabutylammonium fluoride.

17. Method of claim 2 wherein the aminating agent is selected from haloamines, alkylhaloamines, alkenylhaloamines, heteroarylhaloamines and hydroxylamine-O-sulfonic acid.

18. Method of claim 17 wherein the aminating agent is selected from chloramine, allylchloroamine, N-chloroamine, hexyl-chloroamine, butyl-chloroamine, diisobutyl-chloroamine, diethyl-chloroamine, dimethyl-chloroamine, N-chloropiperidine, N-chloropyrrolidine, N-chloromorpholine, N-chlorotetrahydroisoquinoline and hydroxylamine-O-sulfonic acid.

19. A method of preparing sulfonamides of Formula II

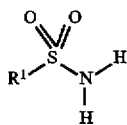
II wherein R¹ is a radical not attached to the sulfur atom through a methylene radical, said method comprising treating a sulfone of Formula III

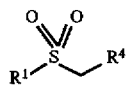
III with a base and an alkylborane in an appropriate solvent to form a trialkylborate-sulfone complex, converting said complex into a sulfinic acid salt, and forming said sulfonamide by treating the sulfinic acid salt with an aminating agent;

wherein R⁴ is selected from hydrido, alkyl, aryl, heteroaryl and alkenyl; and wherein any of the foregoing R¹ and R⁴ groups may be substituted at one or more substitutable positions with one or more radicals independently selected from halo, alkyl, alkoxy, heteroaryl, aryl and cycloalkenyl.

20. A method of preparing sulfonamides of Formula II

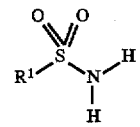
II wherein R¹ is a radical not attached to the sulfur atom through a methylene radical, said method comprising treating a sulfone of Formula III

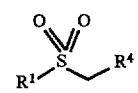
III with a base and an substituted trialkylsilane in an appropriate solvent to form a silylalkylsulfone, treating said silylalkylsulfone with an alkylammonium halide to form a sulfinic acid salt, and forming said sulfonamide by treating the sulfinic acid salt with an aminating agent;

wherein R⁴ is selected from hydrido, alkyl, aryl, heteroaryl and alkenyl; and wherein any of the foregoing R¹ and R⁴ groups may be substituted at one or more substitutable positions with one or more radicals independently selected from halo, alkyl, alkoxy, heteroaryl, aryl and cycloalkenyl.

\* \* \* \* \*